(12) United States Patent
Schnitzspan et al.

(10) Patent No.: US 11,337,781 B2
(45) Date of Patent: May 24, 2022

(54) PRODUCTION METHOD FOR TOOTH REPLACEMENT PART AND VENEER STRUCTURE

(71) Applicant: SIRONA DENTAL SYSTEMS GMBH, Bensheim (DE)

(72) Inventors: Paul Schnitzspan, Seeheim-Jugenheim (DE); Thorsten Jordan, Pfungstadt (DE); Friedemann Roessler, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 323 days.

(21) Appl. No.: 15/742,546

(22) PCT Filed: Jul. 6, 2016

(86) PCT No.: PCT/EP2016/065898
§ 371 (c)(1),
(2) Date: Jan. 8, 2018

(87) PCT Pub. No.: WO2017/005762
PCT Pub. Date: Jan. 12, 2017

(65) Prior Publication Data
US 2018/0200029 A1    Jul. 19, 2018

(30) Foreign Application Priority Data
Jul. 6, 2015   (DE) .................... 10 2015 212 606.4

(51) Int. Cl.
*A61C 8/00* (2006.01)
*A61C 5/70* (2017.01)
(Continued)

(52) U.S. Cl.
CPC .............. *A61C 8/0039* (2013.01); *A61C 5/70* (2017.02); *A61C 8/0048* (2013.01); *A61C 13/34* (2013.01); *G16H 20/40* (2018.01)

(58) Field of Classification Search
CPC ....... A61C 8/0038; A61C 8/0048; A61C 5/70; A61C 13/34; G16H 20/40
See application file for complete search history.

(56) References Cited

U.S. PATENT DOCUMENTS 5,513,989 A * 5/1996 Crisio .................. A61C 8/0086
433/176
5,775,911 A * 7/1998 Hahn .................. A61C 13/0003
264/19
(Continued)

FOREIGN PATENT DOCUMENTS

WO        9313728 A1   7/1993
WO   WO-2014033323 A1 * 3/2014 ........... A61C 8/0074

OTHER PUBLICATIONS

International Search Report; PCT/ EP2016/065898; Oct. 31, 2016 (completed); dated Nov. 16, 2016 (mailed).
(Continued)

*Primary Examiner* — Nicholas D Lucchesi
*Assistant Examiner* — Hao D Mai
(74) *Attorney, Agent, or Firm* — Dentsply Sirona Inc.

(57) ABSTRACT

A method for producing a tooth replacement part to be secured on an implant, based on a 3D model of the tooth replacement part with a surface and with a continuous screw channel with an initial shape in the form of a cylindrical barrel, with a first and a second end, wherein a cross sectional area of the screw channel is designed to be constant and/or to increase in size towards the second end of the screw channel. A 3D model of an inlay with a jacket surface, an upper face and a lower face is generated. A part of the surface of the 3D model of the tooth replacement part that (Continued)

is cut out through the second end of the final shape of the screw channel is used as the upper face and the jacket surface is configured as a negative form of a part of the final shape of the screw channel that adjoins the second end.

5 Claims, 1 Drawing Sheet

(51) Int. Cl.
*A61C 13/34* (2006.01)
*G16H 20/40* (2018.01)

(56) References Cited

U.S. PATENT DOCUMENTS

| | | | | |
|---|---|---|---|---|
| 6,224,371 B1* | 5/2001 | De Luca | ............... | A61C 8/0051 |
| | | | | 264/19 |
| 7,901,209 B2* | 3/2011 | Saliger | ................. | A61C 8/0048 |
| | | | | 433/215 |
| 8,287,278 B2* | 10/2012 | Grant | ..................... | A61C 8/001 |
| | | | | 433/174 |
| 8,403,667 B2* | 3/2013 | Adams | ................... | A61C 8/001 |
| | | | | 433/173 |
| 8,740,616 B2* | 6/2014 | Grant | ................... | A61C 8/0069 |
| | | | | 433/174 |
| 2003/0096214 A1* | 5/2003 | Luthardt | ............ | A61C 13/0004 |
| | | | | 433/171 |
| 2007/0154862 A1* | 7/2007 | Kim | ...................... | A61C 1/084 |
| | | | | 433/72 |
| 2007/0190493 A1* | 8/2007 | Yamamoto | ......... | A61C 13/0004 |
| | | | | 433/221 |
| 2011/0065065 A1 | 3/2011 | Moermann | | |
| 2012/0270179 A1 | 10/2012 | Holmstrom | | |
| 2013/0004917 A1* | 1/2013 | Mayer | .................... | A61K 6/884 |
| | | | | 433/173 |
| 2013/0143178 A1* | 6/2013 | van Ophuysen | ..... | A61C 8/0068 |
| | | | | 433/173 |
| 2013/0209961 A1* | 8/2013 | Rubbert | ................. | A61C 5/007 |
| | | | | 433/175 |
| 2013/0209965 A1* | 8/2013 | Fisker | ...................... | A61C 5/70 |
| | | | | 433/220 |
| 2013/0230827 A1* | 9/2013 | Kwon | .................... | A61C 13/12 |
| | | | | 433/183 |
| 2014/0113251 A1* | 4/2014 | Schweiger | ............... | A61K 6/84 |
| | | | | 433/199.1 |
| 2014/0322664 A1* | 10/2014 | Van Lierde | ............. | G06T 19/20 |
| | | | | 433/72 |
| 2015/0044635 A1 | 2/2015 | Wang | | |
| 2015/0079542 A1 | 3/2015 | Smith | | |
| 2015/0216635 A1 | 8/2015 | Schweiger | | |
| 2016/0030136 A1* | 2/2016 | Hey | ..................... | A61B 5/0088 |
| | | | | 433/75 |

OTHER PUBLICATIONS

International Preliminary Report on Patentability; PCT/ EP2016/ 065898; Oct. 31, 2016 (completed); dated Nov. 16, 2016 (mailed).
Written Opinion of the International Searching Authority; PCT/ EP2016/065898; Oct. 31, 2016 (completed); dated Nov. 16, 2016 (mailed).

* cited by examiner

PRODUCTION METHOD FOR TOOTH REPLACEMENT PART AND VENEER STRUCTURE

TECHNICAL FIELD

The invention relates to a method of a tooth replacement part to be secured on an implant, based on a 3D model of the tooth replacement part, wherein in the 3D model of the tooth replacement part a continuous screw channel for a fixing screw with an initial shape in the form of a cylindrical barrel is generated automatically and/or manually, and a corresponding veneer structure.

BACKGROUND OF THE INVENTION

The prior art discloses a number of ways to secure a tooth replacement part on an implant.

The published document DE 692 15 106 T2 discloses a method for the reconstruction of a dental defect, wherein an oversized and tooth-shaped implant head is secured on an implant and is provided with a relatively thin coating as an outer tooth surface.

US 2003/0096214 A1 describes a method for producing tooth replacement parts with digital processing steps.

WO 2012/052482 A1 discloses a method for providing a patient-specific attachment system for a tooth replacement part, wherein an implant is supplied by means of an abutment, and a tooth replacement part with a corresponding recess is glued to the abutment. The drawback is that the tooth replacement part cannot be removed, for example, in order to check or tighten the screw, without destroying the tooth replacement part.

An easier way to access the screw can be achieved by providing the abutment and the tooth replacement part with a continuous screw channel for a fixing screw, and after fixing the screw, said screw channel is closed by means of a composite filling. By removing the composite, the screw is easily accessible. The drawback is, however, that parts of the abutment and the screw often show through the composite filling; and, as a result, the screw channel appears dark in contrast to the tooth replacement part.

According to US 2015/0079542 A1, this effect can be minimized by constructing the abutment in two parts from a core and a jacket, with the jacket matching the tooth replacement part in color. However, even this design does not prevent the screw head of a fixing screw from showing through the tooth replacement part.

The object of the present invention is to provide an alternative method or, more specifically, a tooth replacement part for the reconstruction of a defect, in order to overcome the aforementioned disadvantages and to further develop the prior art.

SUMMARY OF THE INVENTION

One object of the invention is a method for producing a tooth replacement part to be secured on an implant, based on a 3D model of the tooth replacement part, wherein in the 3D model of the tooth replacement part a continuous screw channel for a fixing screw with an initial shape in the form of a cylindrical barrel, with a first implant-sided end and with a second occlusal or incisal-sided end is generated automatically and/or manually. Then a cross sectional area of the screw channel is designed to be constant and/or to increase in size towards the second end of the screw channel and is stored as the final shape of the screw channel. Then a 3D model of an inlay with a jacket surface, an upper face and a lower face is generated, wherein a part of the surface of the 3D model of the tooth replacement part that is cut out through the second end of the final shape of the screw channel is used as the upper face; and the jacket surface is configured as a negative form of a part of the final shape of the screw channel that adjoins the second end.

It should be noted that the tooth replacement part may be any known veneer structure that is intended for the reconstruction of a dental defect and that is secured by means of a fixing screw. In particular, the tooth replacement part may be a crown or a bridge. The veneer structure may be formed in one piece or in several pieces. The veneer structure may consist, for example, of an abutment and a crown, with the crown containing the screw channel that is to be filled by means of inlays.

Furthermore, it should also be noted that when the cross sectional area of the screw channel remains constant, the original shape is used as a template for the inlay. An increase in size may have any form. That means that the increase in size may be gradual and/or continuous and may affect only individual regions of the circumference of the cross sectional area, so that the shape of the cross section area changes. If the cross sectional area is designed to increase towards the end, then this simply means that at least the cross sectional area of the second end has a larger surface area than the cross sectional area of the first end.

An inlay is defined as a second component that is fitted into a corresponding recess of the veneer structure. This may also be a component, which is usually referred to as an onlay and which occupies a larger area of the lingual and/or palatinal surface of the tooth replacement part, in particular, in the region of the molars.

The inlay can be simply inserted into the screw channel through the cross sectional area of the screw channel that increases in the direction of the incisal, occlusal or oral surface and can be materially bonded so that, for example, the binder cannot be seen on the incisal or occlusal surface.

In order to design the screw channel, a maximum diameter or a circumference of the cross sectional area on the incisal, occlusal or oral surface and/or an increase-defining slope or curve or a length, over which the increase in size is to extend, may be specified in advance or may be queried during the implementation of the method.

The freedom of choice of a user, for example, by drawing or marking points or lines in the 3D model or by defining parameters can be limited by predetermined threshold values or boundary conditions. For example, a minimum value for the slope, a maximum value for the length, over which the increase may extend, or a minimum increase in the cross sectional area may be stored.

Filling the screw channel with an inlay ensures that the color scheme of the incisal, occlusal or oral surface of a final veneer structure consisting of tooth replacement part and inlay is uniform; and, in particular, the color of the area above the screw channel matches the color of the rest of the surface of the tooth replacement part.

One advantage of the method of the invention is that simultaneously easy accessibility of the fixing screw by removing the inlay and without destroying the rest of the tooth replacement part is ensured, and a surface, which is as much like a natural tooth as possible and has a uniform color, is achieved.

Advantageously, in order to design the increase in size of the screw channel on the surface of the 3D model of the tooth replacement part, a line, which encloses the cylindrical initial shape of the screw channel in the circumferential direction, is generated automatically and/or manually; a slope or a length of the increase in size is specified automatically and/or manually; and the final shape of the screw channel is designed with the specified slope or to increase in size beyond the specified length as far as up to the line. This arrangement allows a user to easily design or reconstruct the increase in the cross sectional area of the screw channel.

Advantageously, the jacket surface of the 3D model of the inlay is moved automatically and/or manually at least partially in the direction of a longitudinal axis of the 3D model of the inlay. In this way a veneer structure, composed of a tooth replacement part and inlay, has a gap for a binder, for example, an adhesive.

Advantageously, in order to secure against rotation, the cross sectional area of the screw channel in the region of the increase in size is configured with a non-rotationally symmetrical shape that is unique in the circumferential direction. A circumferential line of the cross sectional area of the screw channel in the region of the second end may have, for example, a concave curvature, which deviates from the circular shape of the initial shape in the form of a cylindrical barrel.

The term "unique" or "non-rotationally symmetrical" means in this context a shape or configuration of the cross sectional area that ensures that when the inlay is inserted into the screw channel, the inlay is properly positioned with respect to a rotation about a longitudinal axis of the screw channel, so that the surface of the tooth replacement part and the inlay complement each other to create a surface that resembles a tooth as much as possible.

Furthermore, the invention relates to a veneer structure for the reconstruction of a dental defect, said veneer structure consisting of a tooth replacement part with a continuous screw channel for a fixing screw; the screw channel at least in a region adjoining an incisal or occlusal second end of the screw channel has a constant and/or increasing cross sectional area towards the incisal, occlusal or oral region. Furthermore, the veneer structure comprises an inlay with an upper face, a lower face and a jacket surface, wherein the jacket surface corresponds to a negative form of a part of the screw channel that adjoins the incisal, occlusal or oral surface; and the upper face represents a continuation of the incisal, occlusal or oral surface in the region of the screw channel.

The advantage of the veneer structure of the invention is the easy accessibility of a fixing screw that secures the veneer structure on the implant, on the one hand, and, on the other hand, the guarantee of a uniform color and/or an appearance of the entire surface of the veneer structure that adequately resembles a tooth.

Advantageously, the screw channel in the region, adjoining the second end, has a shape that is unique in the circumferential direction and that ensures an orientation between the tooth replacement part and the inlay that is unique in the circumferential direction.

BRIEF DESCRIPTION OF THE DRAWINGS

Exemplary embodiments of the invention are shown in the drawings. The drawings show in FIG. 1 a 3D model of a tooth replacement part, and
FIG. 2 an inlay to complement the tooth replacement part.

DETAILED DESCRIPTION OF THE INVENTION

Figure 1:
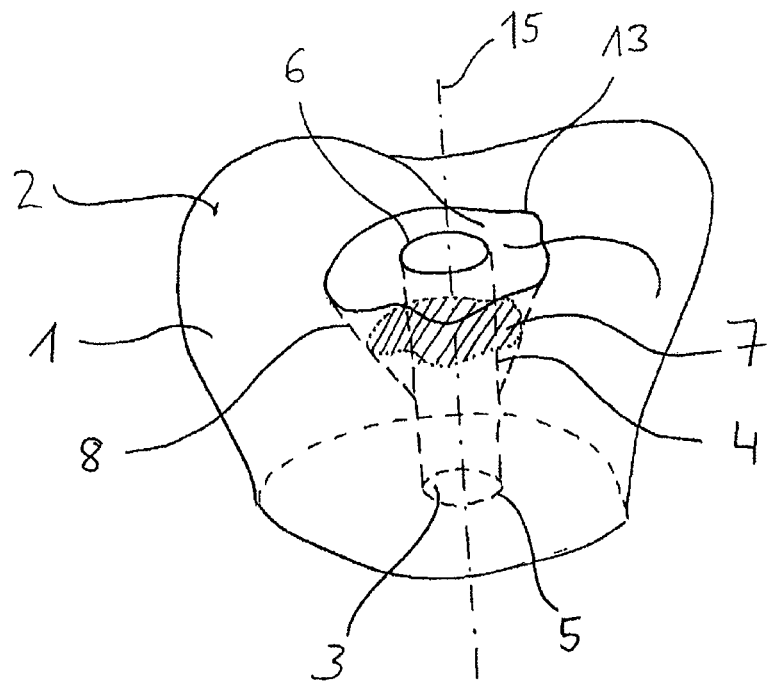

FIG. 1 is a schematic representation of a 3D model of a tooth replacement part 1 for a CAM based fabrication of a tooth replacement part, to be secured on an implant (not shown), for a molar. The 3D model of the tooth replacement part 1 has a surface 2 consisting of an occlusal surface, side faces and a lower face, wherein, in particular, the occlusal surface and the side faces already have the desired shape or structure of a final veneer structure for reconstructing a dental defect. A screw channel 3 for a fixing screw (not shown) passes through the 3D model of the tooth replacement part 1 from the lower face as far as up to the occlusal surface.

The screw channel 3 is generated manually and/or automatically and has an initial shape 4 in the form of a cylindrical barrel, with a first implant-sided end 5 and a second occlusal-sided end 6. In order to generate the initial shape 4, it is necessary to consider, in particular, the implant axis of the implant, to be supplied with the tooth replacement part, and a diameter of the fixing screw.

Starting from the initial shape 4, a final shape 8 of the screw channel 3 is generated, where in this case said final shape has a cross sectional area 5 that increases in the direction of the second end 6, i.e., in the direction of the occlusal surface. For this purpose, a line 13, which completely encloses the second end 6 of the screw channel, is drawn automatically and/or manually, for example, by means of an input means, such as, a computer mouse, on the occlusal surface of the 3D model of the tooth replacement part 1. The line may be circular with a diameter that is larger than the diameter of the initial shape 4 in the form of a cylindrical barrel. In order to provide a connecting geometry, which is unique in the direction of rotation about a longitudinal axis 15 of the screw channel 3, the line may also have an undulatory and non-rotationally symmetrical contour, as shown in FIG. 1.

Then the contour of the final shape 8 of the screw channel 3 is produced in that the initial shape in the form of cylindrical barrel is expanded at least in the region of the second end 6 as far as up to the line 13, so that the line 13 forms the second end 6 of the screw channel 3. For this purpose a fixed slope value, a slope gradient, or also a length, over which the expansion or, more specifically, the increase in size towards the second end 6 should extend, is set in advance and/or by the input of a user. The resulting screw channel 3 having a cylindrical barrel-shaped beginning in the region of the first end 5 and an end, which increases, for example, in the shape of a truncated cone, in the region of the second end 6 is stored as the final shape 8.

Figure 2:
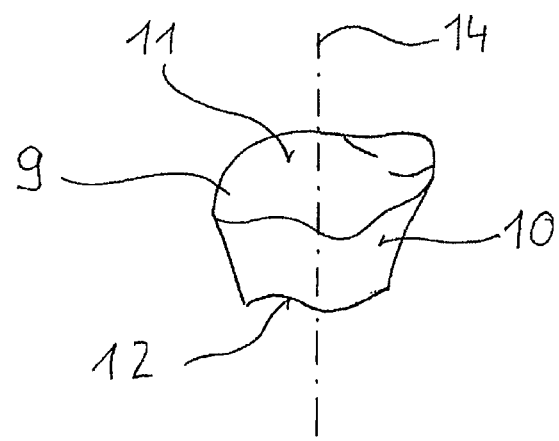

Then a 3D data record of an inlay 9, which fits into the second end 6 of the screw channel 3, is generated on the basis of the final shape 8 of the screw channel 3, as shown in schematic form in FIG. 2. For this purpose a part of the surface that is cut through the second end 6 of the screw channel 3 out of the occlusal surface of the 3D data record of the tooth replacement part 1, is used as an upper face 11. A jacket surface 10 of the inlay 9 is configured as a negative form of a part of the final shape 8 of the screw channel 3 in the region of the second end 6 and is supplemented by a lower face 12 terminating the inlay.

By generating automatically or by means of predetermined boundary conditions when manually generating the final shape 8 of the screw channel 3 and generating the inlay 9 it can be ensured that the finished tooth replacement part 1 together with the inlay 9 meets the desired requirements of aesthetics, stability and durability. For example, by specifying a minimum value for the length, over which the increase in size of the screw channel 3 extends, it can be ensured that the inlay, to be fitted therein, has a sufficient height or thickness, in order to be fabricated from a desired material and to meet the color or aesthetic requirements.

In order to be able to ensure a secure hold of the inlay in the screw channel 3, the jacket surface 10 may be moved, as indicated by the dashed line in FIG. 2, at least partially in the direction of a longitudinal axis 14 of the inlay 9 in a subsequent process step. In this way a gap for a binder, for example, an adhesive, is formed upon insertion of the inlay 9 into the tooth replacement part 1.

LIST OF REFERENCE NUMERALS

1 3D model of the tooth replacement part
2 surface of the 3D model of the tooth replacement part
3 screw channel
4 initial shape of the screw channel
5 first end of the screw channel
6 second end of the screw channel
7 cross sectional area of the screw channel
8 final shape of the screw channel
9 inlay
10 jacket surface of the inlay
11 upper face of the inlay
12 lower face of the inlay
13 line
14 longitudinal axis of the inlay
15 longitudinal axis of the screw channel

The invention claimed is:

1. A computer-implemented method for producing a veneer structure that includes an inlay and a tooth replacement part to be secured on an implant, based on a virtual 3D model of the tooth replacement part having a surface, comprising the steps of:

virtually generating in the virtual 3D(three-dimensional) model of the tooth replacement part, a virtual screw channel for a fixing screw with an initial shape in the form of a cylindrical barrel, with a first implant-sided end and with a second occlusal or incisal-sided end being generated automatically or manually, virtually designing a cross sectional area of the virtual screw channel to increase in size towards the second end of the screw channel such that at least a cross sectional area of the second end has a larger surface area than a cross sectional area of the first end, wherein a resulting shape is stored as a final shape of the virtual screw channel; and virtually designing a virtual 3D model of an inlay that corresponds to a negative form of a part of the final shape of the virtual screw channel at the second end, wherein the virtual 3D model of the inlay is virtually designed to have an virtual upper face, a virtual lower face and a virtual jacket surface extending therebetween, and responsive to the virtually generating and designing steps being completed, manufacturing the veneer structure based on 3D data of the virtual 3D model of the tooth replacement part and the virtual 3D model of the inlay.

2. The computer-implemented method, as claimed in claim 1, wherein to virtually design the increase in size of the screw channel on the surface of the 3D model of the tooth replacement part, a line, which encloses the initial shape of the screw channel in a circumferential direction, is generated manually of automatically;

a slope or a length of the increase in size is specified automatically or manually; and the final shape of the screw channel is designed with the slope or to increase in size beyond the length up to the line.

3. The computer-implemented method, as claimed in claim 1, wherein the jacket surface of the 3D model of the inlay is moved automatically or manually at least partially hi the direction of a longitudinal axis of the 3D model of the inlay.

4. The computer-implemented method, as claimed in claim 1, wherein the cross sectional area of the screw channel in the region of the increase in size is virtually designed to have a non-rotationally symmetrical shape that is unique in the circumferential direction, in order to secure against rotation.

5. The computer-implemented method of claim 1, wherein the inlay of the produced veneer is configured to be different from and seated on the fixing screw, and wherein the fixing screw is accessible by removing the inlay so that a rest of the tooth replacement part is not destroyed.

* * * * *